United States Patent
Dance et al.

[19]

[11] Patent Number: 6,113,576
[45] Date of Patent: Sep. 5, 2000

[54] THROMBOLYSIS CATHETER SYSTEM WITH FIXED LENGTH INFUSION ZONE

[75] Inventors: Creg W. Dance, Elk River; Steven L. Olson, Isanti, both of Minn.

[73] Assignee: Lake Region Manufacturing, Inc., Chaska, Minn.

[21] Appl. No.: 08/101,989

[22] Filed: Aug. 4, 1993

[51] Int. Cl.[7] .................................................. A61M 5/178
[52] U.S. Cl. ........................................... 604/164; 604/528
[58] Field of Search .............................. 604/96, 101, 49, 604/53, 102, 164, 165, 249, 256, 528, 523; 606/194

[56] References Cited

U.S. PATENT DOCUMENTS

| | | | |
|---|---|---|---|
| 4,922,924 | 5/1990 | Gambale et al. | 604/164 |
| 5,046,503 | 9/1991 | Schneiderman | 604/102 |
| 5,085,635 | 2/1992 | Cragg | 604/102 |
| 5,090,960 | 2/1992 | Don Michael | 604/101 |
| 5,219,335 | 6/1993 | Willard et al. | 604/96 |
| 5,250,034 | 10/1993 | Appling et al. | 604/256 |
| 5,279,546 | 1/1994 | Mische et al. | 604/101 |

*Primary Examiner*—Mark O. Polutta
*Assistant Examiner*—Jeremy Thissell
*Attorney, Agent, or Firm*—Grady J. Frenchick; Michael Best & Friedrich LLP

[57] ABSTRACT

A thrombolysis catheter system having a fixed length infusion zone is disclosed. The invention contemplates apparatus, method and kit aspects. The apparatus, which has the capability to track a guidewire, uses a multilumen catheter to deliver radially thrombolytic agent to an infusion zone defined by one or more balloon means. In one aspect, with an occluder means, a primary lumen of the catheter is used both for catheter placement and delivery of fluid. The method discloses utilization of radiopaque indicia to place the catheter in proximity to the occlusion or diseased tissue to be treated. The kit includes a catheter of the invention in conjunction with a steerable guidewire and a tip occluder wire, either or both of the tip occluder wire and the guidewire having an enlargement on their distal tip which cooperates with a reduced diameter portion of the catheter lumen.

1 Claim, 8 Drawing Sheets

THROMBOLYSIS CATHETER SYSTEM WITH FIXED LENGTH INFUSION ZONE

BACKGROUND OF THE INVENTION

1. Field of the Invention

This invention relates generally to devices used to clear obstructions in body passageways, more particularly, this invention relates to apparatuses and methods of treating such obstructions by the infusion of chemical thrombolytic agents. Yet more particularly, this invention relates to catheters and to catheter systems for exposing vascular obstructions to therapeutic agents, generally to effectuate their removal.

2. Description of the Prior Art

The use of catheter systems to treat various medical conditions has been known for some time. In treating a particular area within a body passageway, it is often desirable to isolate the area to be treated from the rest of the body. One approach to isolating a treatment area is the placement of one or more inflatable balloons proximal or distal (or both) to the treatment area. Inflating the balloon or balloons serves to isolate the vascular structure to be treated and permits control of the length of time of exposure. U.S. Pat. No. 2,936,760 issued to Gants, U.S. Pat. No. 4,022,216 issued to Stevens, and U.S. Pat. No. 4,705,502 issued to Patel describe catheters designed for use in the urinary tract.

Catheter systems are also used in other applications. U.S. Pat. No. 4,696,668 issued to Wilcox, for example, describes a catheter system for treatment of nasobiliary occlusions. Similarly, U.S. Pat. No. 4,198,981 issued to Sinnreich is used in intrauterine applications. U.S. Pat. No. 4,453,545 issued to Inoue discloses an endotracheal tube.

One of the most common applications for catheter systems is the treatment of occlusions within the cardiovascular system. A catheter system for venous applications is seen in U.S. Pat. No. 4,795,427 issued to Helzel. U.S. Pat. No. 4,636,195 issued to Wollinsky, U.S. Pat. No. 4,705,507 issued to Boyles, and U.S. Pat. No. 4,573,966 issued to Welkl et al., all describe catheter systems designed to infuse a liquid for the treatment of an arterial occlusion. Each of these devices has one or more balloons which can be inflated to occlude the artery during the treatment process.

U.S. Pat. No. 4,655,746 issued to Daniels et al. discloses the use of two concentric catheters defining an interlumenal space therebetween. Each of the catheters has its own balloon to isolate (adjustably) a portion of the body passageway. The Daniels et al. design, however, requires the use of the interlumenal space as a fluid passageway, thereby complicating the construction and operation of the device.

U.S. Pat. No. 4,927,418 to Dake et al. discloses a catheter for uniform distribution of therapeutic fluids. The Dake et al. catheter utilizes a relatively thick-walled tubular body having a plurality of smaller lumens therein in conjunction with a larger central lumen discharging fluid from the catheter.

U.S. Pat. No. 5,059,178 to Ya uses balloons to subtend a blood vessel upstream and downstream of a thrombus. Thrombus dissolving agent is supplied to the zone between the balloons. An expansion catheter having a third balloon is used to expand a location of structure remaining after removal of the dissolved thrombus.

BRIEF SUMMARY OF THE INVENTION

The present invention provides an apparatus, a method, and a kit for treating an obstruction in a body passageway, such as a vein or an artery, through the infusion of a fluid. In one aspect the present invention is a catheter for administering therapeutic agent to an obstruction within a vascular system. A catheter of this invention has a fixed length infusion zone generally defined by one or more inflatable balloons and a series of infusion orifices located therebetween. A catheter of this invention comprises a cylindrical catheter body. The cylindrical catheter body comprises a wall, the wall having distal and proximal ends. One of the distal or proximal segment ends of the catheter wall body has a balloon means located thereon. The wall further includes or defines a plurality of radial orifices.

The catheter body also interiorly defines a primary lumen, the primary lumen extending through the catheter body to couple, fluidically, the orifices and its distal and proximal ends. The primary lumen has a larger diameter segment beginning adjacent the proximal end of the catheter and extending the majority of the length of said catheter body, and a smaller diameter segment located interiorly adjacent the distal end of the catheter body and distal to the orifices. The reduced diameter segment of the primary lumen is adapted to cooperate with a separate occluder means (described below) to restrict fluid flow out the distal end of the first lumen and to force such fluid to flow radially from the orifices. The diameter of the primary lumen, with the exception of the extreme distal portion, is in the range of about 0.16 inches to about 0.065 inches while the diameter of the smaller diameter segment is in the range of about 0.014 inches to about 0.060 inches.

The catheter body of a catheter of this invention, preferably, also defines at least a second lumen, the second lumen being in fluid communication with the balloon means and the proximal end of the catheter body so as to permit said balloon means to be inflated therefrom. The diameter of any second lumens is in the range of about 0.009 inches to about 0.025 inches.

In a preferred practice of this invention, two balloons are used to isolate the treatment area from the remainder of the body so that therapeutic agent may be infused therearound. One of each of the balloons is located on the catheter wall upstream and downstream of the infusion ports.

In another aspect, the present invention is a method of treating an obstruction, such as thrombus, within a vascular structure. (The location of the obstruction has been previously identified by methods well known to this art.) A method according to this invention comprises the steps of first advancing a steerable guidewire through the vasculature until the distal tip thereof is adjacent i.e., in the vicinity or proximate to, the previously located obstruction or diseased segment to be treated. Next, a catheter having a structure as described above is advanced or slid over the guidewire until the infusion zone is located at the treatment site. At this juncture, the spatial relationship between the obstruction and the catheter/guidewire structure will determine the next step. If the steerable guidewire/catheter combination/structure cannot be positioned through the obstructed segment, then the guidewire is removed from the catheter and an occlusion means, occlusion wire, or tip occluder wire, is advanced through the primary lumen thereof. If the catheter/guidewire combination structure can be passed through the vascular obstruction, utilization of the steerable catheter guidewire/combination continues. While utilization of the steerable wire is preferred, a non-steerable tip occluder wire permits the extreme distal portion of the catheter to be positioned more closely to, for example, thrombus which cannot be crossed with a steerable wire. Withdrawing a steerable guidewire from the catheter body, which would permit the catheter to be positioned more closely to the treatment site, tends to restrict radial fluid delivery due to restriction of diameter of the primary lumen. Both the steerable guidewire and the occlusion means or tip occluder wire have an enlargement adjacent their distal ends which cooperates with the reduced diameter portion of the primary lumen substantially to prevent fluid from passing distally from the catheter.

Whether the tip occluder or steerable guidewire is used, the next step is to inflate the balloon means to define the treatment area. Lastly, thrombolytic agent is introduced into the primary lumen and subsequently exits or infuses from the radial passages to the infusion zone to treat the obstruction. Additional therapeutic procedures may be performed following the above-described method.

In a preferred practice of this method, the catheter includes a plurality of balloons located distally and proximally with respect to the orifices. The balloons are fluidically coupled to the proximal end of the catheter by means of secondary lumens which permit the balloons thereby to be inflated and deflated. Thrombolytic agents may include urokinase, streptokinase, tissue plasminogen activator (TPA), or a similar therapeutic species. As the lesion within the treatment area is exposed to the thrombolytic agent, some of the material is dissolved and is removed therefrom.

In a preferred practice of the above method, a radiopaque structure on the catheter, usually on its distal segment, is monitored while the catheter is positioned within the vasculature. A plurality of radiopaque structures, such as platinum rings or bands, may be disposed along the length of the catheter, and on the steerable guidewire and on the occluder wire. These structures appear more intense than adjacent, non-radiopaque materials under fluoroscopic examination. Generally, a steerable guidewire will have a radiopaque distal tip and possibly additional proximally-located radiopaque structures. By observation of these radiopaque structures, the progress of the catheter into the vasculature can be observed, the location of the balloon or balloons (and therefore the infusion zone) relative to the treatment site can be determined, and the relationship between the catheter and the guidewire or occluder wire can be monitored. Utilization of the cooperatively located radiopaque structures in catheter placement and in therapeutic application is a particularly advantageous aspect of the present methods.

Yet a further aspect of this invention comprises a kit. A kit of this invention comprises an occluder means such as a tip occluder wire having an enlargement adjacent its distal end and a steerable guidewire. The guidewire preferably has an enlargement adjacent its distal end, thereby incorporating the features of both a steerable guidewire and a non-steerable occluder wire. The diameter of the enlargement of either or both of the guidewire or occluder wire is determined by the interior diameter of the reduced diameter segment of the primary lumen of the catheter. A kit having at least the above three components offers medical personnel employing a catheter of this invention the ability to maximize their options with respect to patient treatment. Kit components may include other necessary or desirable equipment such as stopcocks, syringes and gloves.

BRIEF DESCRIPTION OF THE DRAWINGS

Other objects of the present invention and many of the attendant advantages of the present invention will be readily appreciated as the same become better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
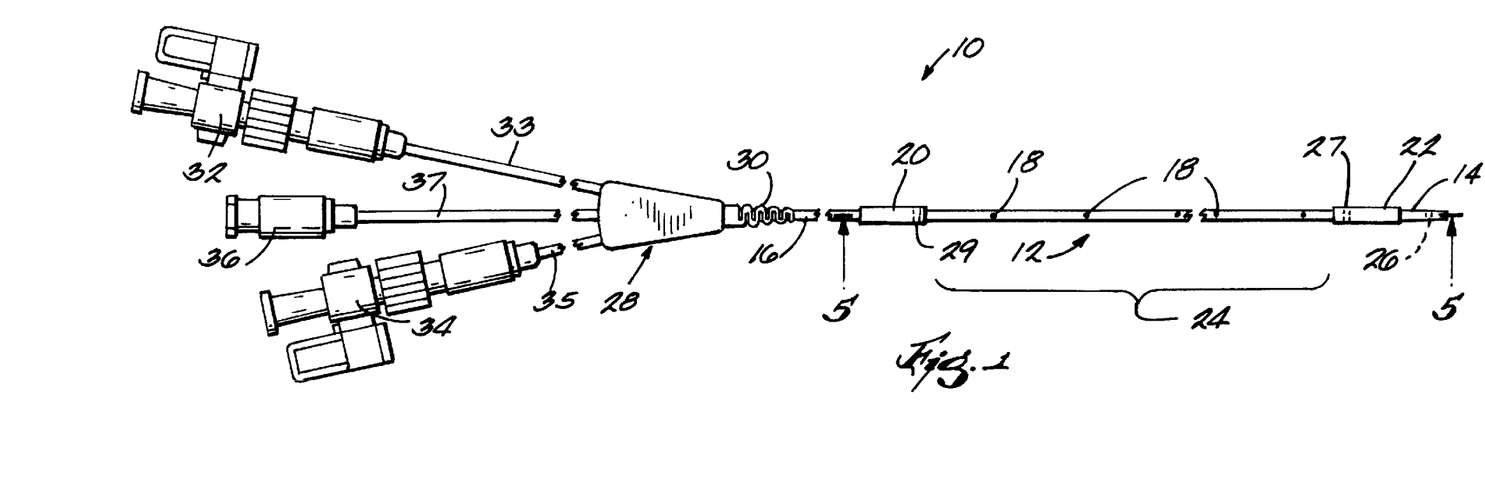
FIG. 1 is a plan view of a catheter of the present invention.

FIG. 1 is a plan view of a thrombolysis catheter or catheter system 10 of the present invention. Catheter 10 comprises a cylindrical catheter body 12. Catheter body 12 is flexible so as to be able to negotiate tortuous vascular structures and has distal and proximal ends 14, 16 respectively. For purposes of reference herein, the terms "distal" and "proximal" are determined from the frame of reference of a user. Thus a "proximal" structure or indication tends to be located closer to the user. Catheter body 12 has therein (and defines) a plurality of radial orifices 18. Catheter body 12 also has located on its external surface proximal and distal balloons 20, 22, respectively. Balloons 20, 22 are shown in their deflated state, i.e., substantially as they would appear as the catheter is being deployed within a patient's vasculature.

Between balloons 20, 22 is an infusion zone or operating segment 24. Infusion zone 24 is the working or operating portion of the catheter system of this invention in the sense that, after vascular manipulation and positioning, this portion of the system will be located adjacent the restriction or occlusion to be treated. Generally this will mean that the operating segment of the catheter will be located upstream from, or across (through) the restriction. Illustrating this practice of the invention, balloons 20, 22 will be located upstream and downstream, respectively, of the occlusion or tumorous structure to be treated, if a catheter system having two balloons is utilized.

Also illustrated in FIG. 1 is an optional radiopaque marker band 26. Marker band 26 generally comprises a substantially radiopaque material such as platinum and platinum alloys.

Marker band 26 is disposed on the distal end 14 of the catheter body 12 so that it can be observed fluoroscopically during catheter placement. In this manner, attending medical personnel can determine where catheter distal segment 14 is located relative to the previously identified site of the vascular obstruction. Moreover, depending upon the application, a plurality of marker means or marker bands may be employed, to provide even more information to attending medical personnel as to where various catheter structures are located within the vasculature. For example, marker bands 27 and 29 (shown in phantom in FIG. 1 because they are beneath the balloons) indicate the approximate positions of proximal and distal balloons 20, 22.

Radiopaque marker bands may be flush with the external surface of catheter body 12 or they may lie above or within it. The proximal end 16 of catheter body 12 is coupled to a trilumen connector 28 the details of which are more completely discussed below. Trilumen connector 28 is coupled to catheter body proximal end 16 via strain reliever 30. Connector 28 couples to a plurality of luer stopcock connectors 32, 34 which are fluidically connected, via tubes 33, 35 and catheter body luminae, to balloons 20, 22. Axial luer port connector 36 is coupled (via tube 37) to catheter body 12 and, in turn, to its principal lumen, the details of which are discussed below.

Figure 2:
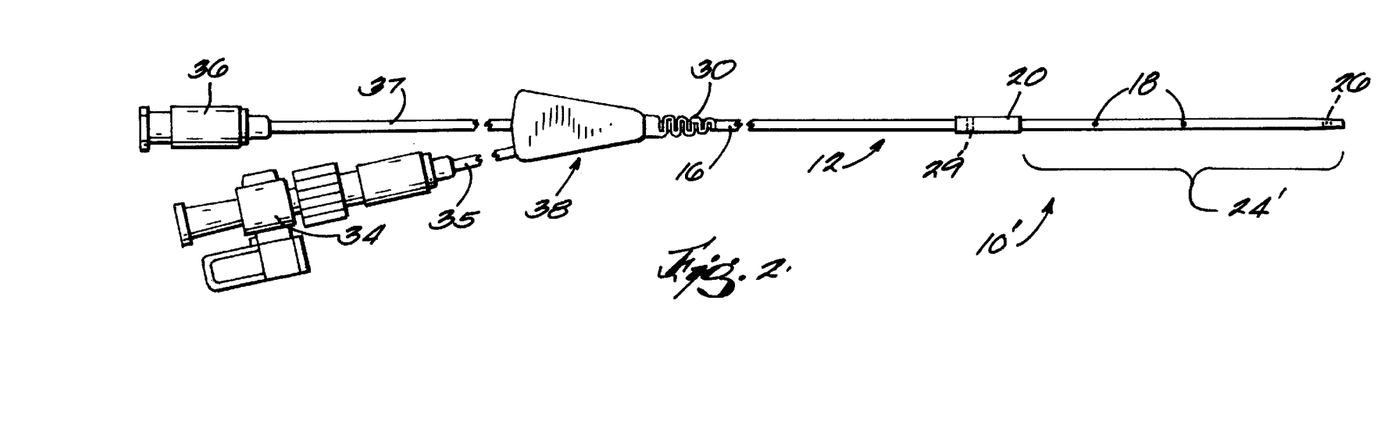
FIG. 2 is a plan view of a second embodiment of a catheter of the present invention.

FIG. 2 illustrates an embodiment of the invention in which there is a single proximal balloon 20. Located distally with respect to proximal balloon 20 is infusion zone 24'. Infusion zone 24', in this embodiment, includes radiopaque marker band 26 which generally indicates one of its edges. Infusion zone 24' has no distally located balloon and therefor has only a single luer coupler 34. Further, the catheter of FIG. 2 has a bilumen connector 38 which fluidically couples to catheter body 12. Infusion zone 24', in this embodiment, is relatively short. Infusion zones generally have a length in the range of about ½ inch to about 10 inches. The length of the infusion zone selected will depend upon the intended therapy, the number of orifices, the therapeutic agent to be infused, the intended infusion rate, whether one or two balloons are to be employed on the catheter, and the extent to which distal migration of thrombolytic agent/dissolution products is to be permitted.

Figure 3:
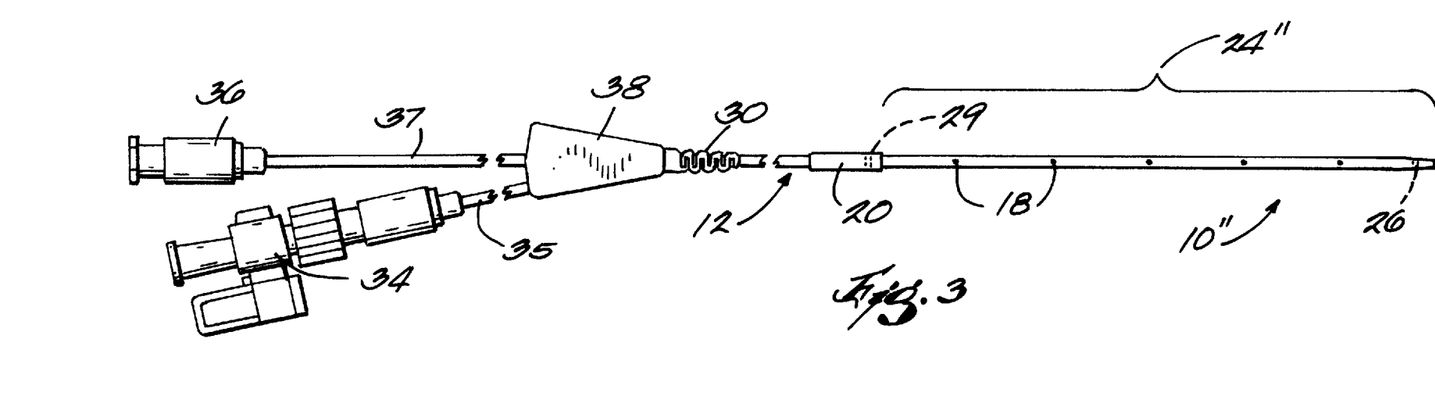
FIG. 3 is a view of a catheter of this invention with an infusion zone proximal to the balloon.

FIG. 3 illustrates a catheter of this invention substantially the same as FIG. 2 but having a substantially longer infusion zone 24".

Figure 4:
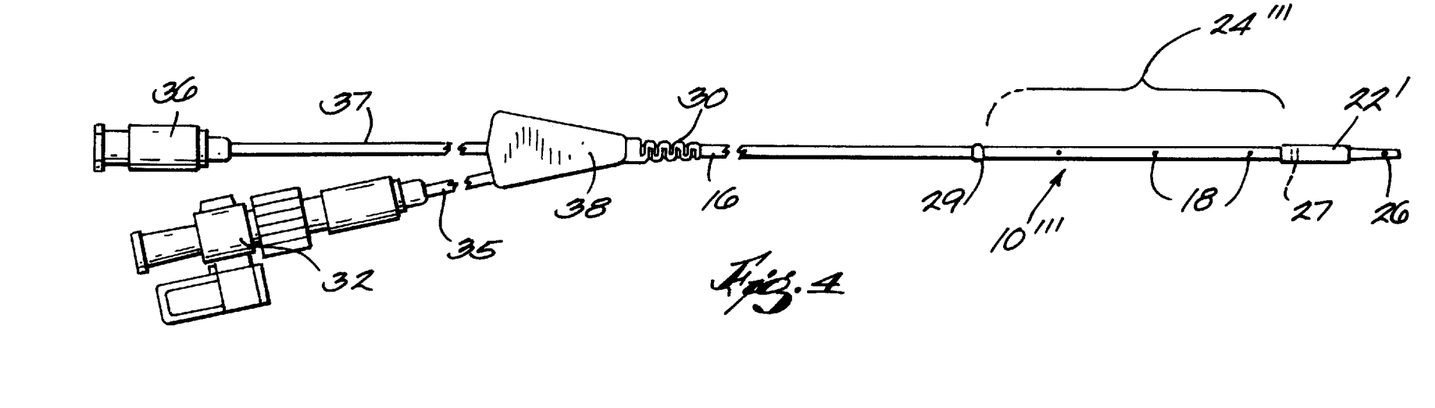
FIG. 4 is a view of a catheter of this invention with an infusion zone distal to the balloon.

FIG. 4 illustrates an embodiment of the invention 10''' in which a single balloon 22' is located distally, i.e., downstream, with respect to infusion zone 24'''. The following edge or proximal limit of infusion zone 24''' is shown as a dotted line because the proximal limit is not more precisely defined by a proximal balloon. In other words, the proximal limit or edge of infusion zone 24''', in this embodiment 10''', with only a distal balloon 22' will lie upstream of orifices 18 but will not be as precisely defined as if two balloons were utilized. Radiopaque proximal marker band 29 indicates, under fluoroscopic observation, the approximate proximal or upstream limit of infusion zone 24'''.

Figure 5:
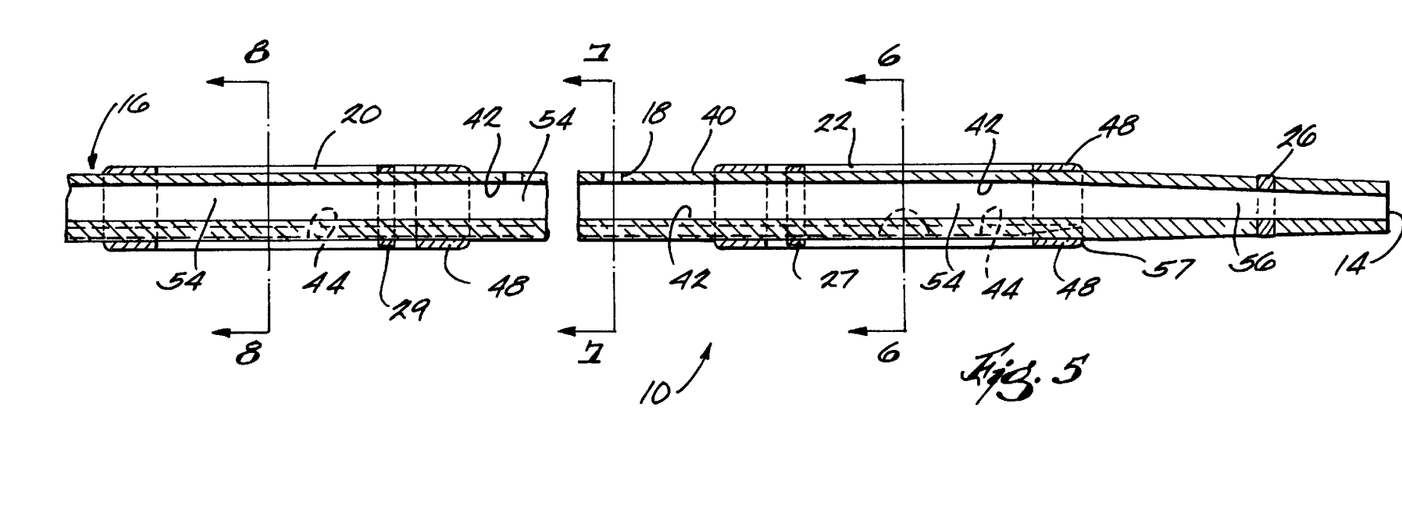
FIG. 5 is a sectional view of the catheter body taken alone line 5—5 of FIG. 1.

FIG. 5 is a detailed sectional view of the embodiment of FIG. 1 taken along line 5—5 of FIG. 1. Catheter body 12 is shown to have a catheter body wall 40. Catheter body wall 40 defines a slightly off-axis principal lumen 42. Catheter body wall 40, in this embodiment, defines two additional smaller diameter secondary lumens 44, 46 one of which is shown in phantom in FIG. 5 and both of which are better shown in FIGS. 6–8. Proximal and distal balloons 20, 22 are exteriorly affixed to catheter wall body 40, e.g., by adhesive indicated at 48. Orifice 18 is shown to be in communication with principal lumen 42 so that fluid input from the proximal end of the device (generally to the left in FIG. 5), after passing through principal lumen 42 would be radially dispensed therefrom. Distal, medial and proximal radiopaque marker bands 26, 27 and 29, respectively, are externally disposed on catheter body wall 40 so that the tip of the device and the balloon locations can all be fluoroscopically monitored during catheter system placement and utilization.

Principal lumen 42 has a larger diameter, proximal segment 54 and a smaller diameter, distal segment 56'. Smaller diameter principal lumen segment 56 is of a size such that an occluder segment or a steerable guidewire can be inserted therein and substantially stop proximal fluid flow out catheter body distal end 14. By passing, for example, an nonsteerable occluder wire or a steerable guidewire having an enlargement down principal lumen 42, lumen 42 is occluded and distal fluid flow prevented. This forces fluid entering principal lumen 42 at catheter body proximal end 16 to exit radially from, e.g., orifice 18. In this manner, catheter system 10 can be directed to the site of a vascular occlusion and (after inflating the balloons) thrombolytic treatment applied.

Principal lumen reduced diameter segment 56, as shown, begins to taper in diameter at about the leading edge 57 of distal balloon 22. Reduction or tapering in diameter permits a larger range of occluder wire or guidewire enlargements to be employed. Also, if a guidewire or occluder wire enlargement is somewhat compressible, a more fluid-tight fit can be formed with the tapering lumen interior wall.

Figure 6:
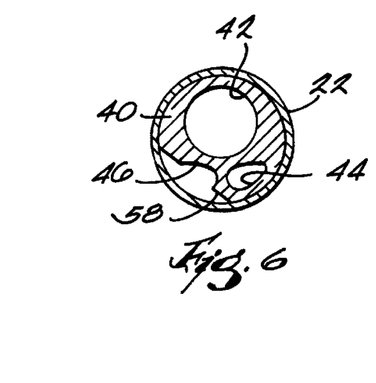
FIGS. 6, 7 and 8 are sectional views of the catheter body distal segment taken along lines 6—6, 7—7, and 8—8, respectively.
Figure 7:
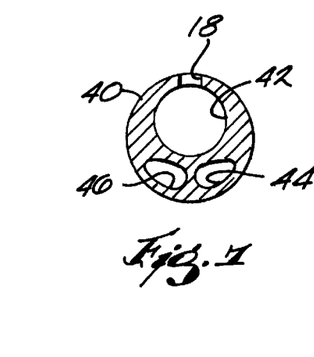
Figure 8:
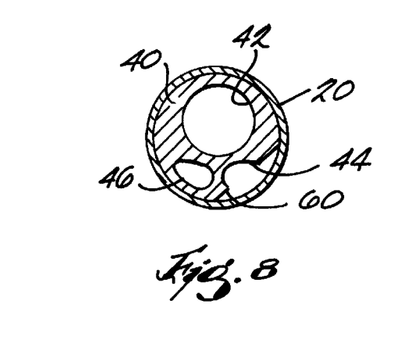

FIGS. 6, 7, and 8 illustrate the internal details of catheter body 40 which define some of the important features of this invention. Deflated distal balloon 22 and proximal balloon 20 are shown in FIGS. 6 and 8, respectively. Such balloons would be fashioned from a stretchable, inflatable material such as latex. By means of an opening or skive 58, distal balloon 22 is in fluid communication with secondary lumen 46. Proximal balloon 20 is in fluid communication with secondary lumen 44 via a second proximal skive 60. Secondary lumens 44 and 46 are in fluid communication with catheter proximal end 16 so that, by means of proximal valves or couplers, discussed in greater detail below, the balloons may be separately and independently inflated and deflated therefrom, e.g., with external fluid sources.

Skives 58 and 60 may be simply cut or drilled into catheter body wall 40. Principal lumen 42 and secondary lumens 44, 46 may be simultaneously formed, e.g., by extrusion of catheter body 12 of a thermoforming polymeric material. Various catheter body materials have been found to be usable to produce catheter bodies. Extrudable polyester elastomer materials as well as vinyl polymer materials are preferred.

Figures 9, 10:
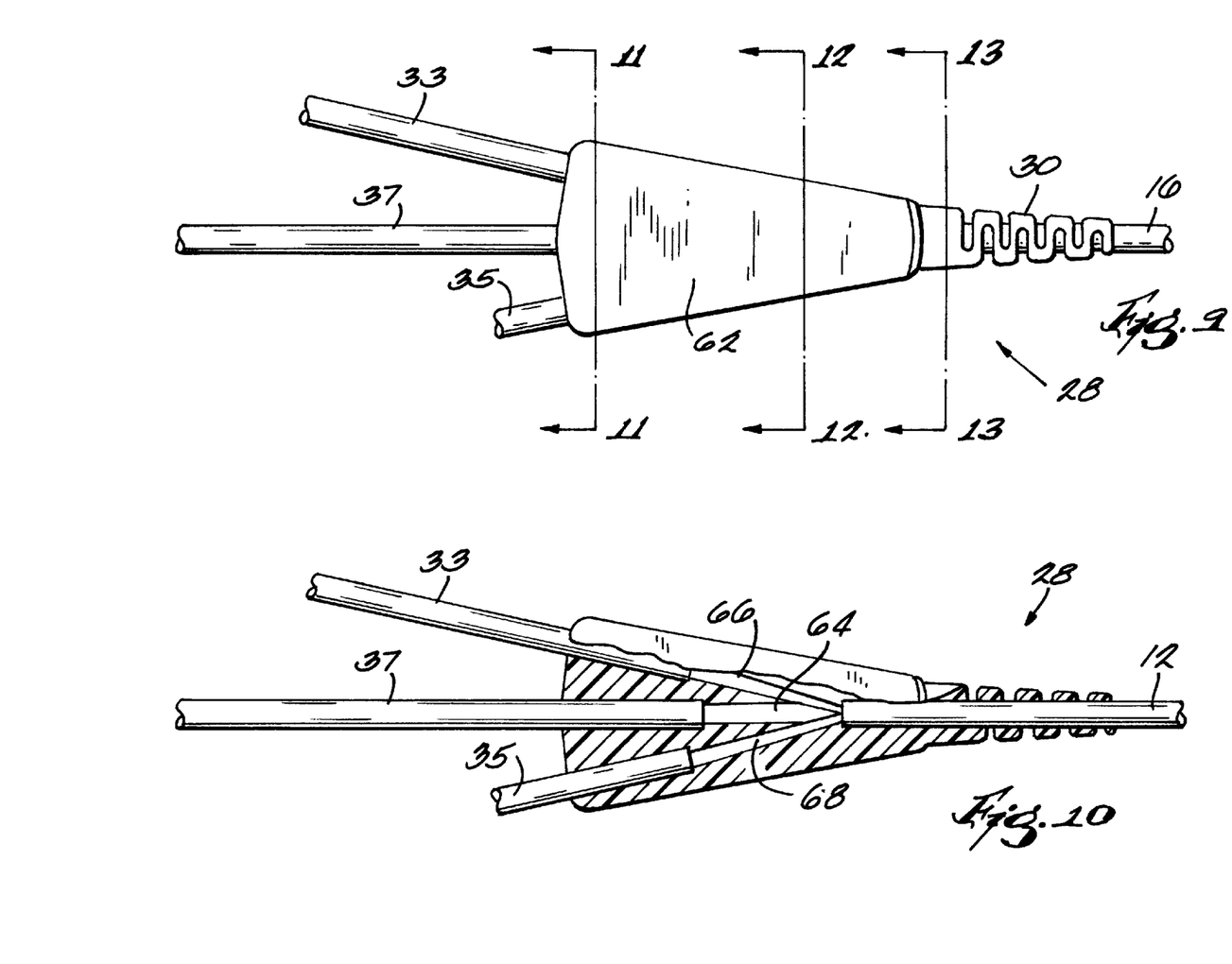
FIG. 9 is a perspective view of the proximal end connector of a catheter of this invention.
FIG. 10 is a view of the proximal end connector of FIG. 9 with parts cut away and shown in section.

FIGS. 9 and 10 illustrate in plan view and in partial sectional view, the details of trilumen connector 28. Trilumen connector 28 is disposed adjacent the proximal end of catheter body 12. As shown in the external view of FIG. 9, trilumen connector 28 comprises a triangularly shaped connector body 62. Connector body 62 may be planar (as shown) or it may be curvilinear with the axes of the lumens being non-planar. Connector body 62 couples with catheter body 12 by means of strain reliever 30. Connector body 62 has molded or machined therein three separate channels 64, 66, and 68 respectively. Channels 64, 66, and 68 are coupled to input tubes 33, 35 and 37, respectively. While the coupling of input tubes 33, 35 and 37 with respect to channels 64, 66 and 68 is not critical, as shown, tube 33 leads to channel 64, tube 35 leads to channel 66, and tube 37 leads to channel 68.

Figure 11:
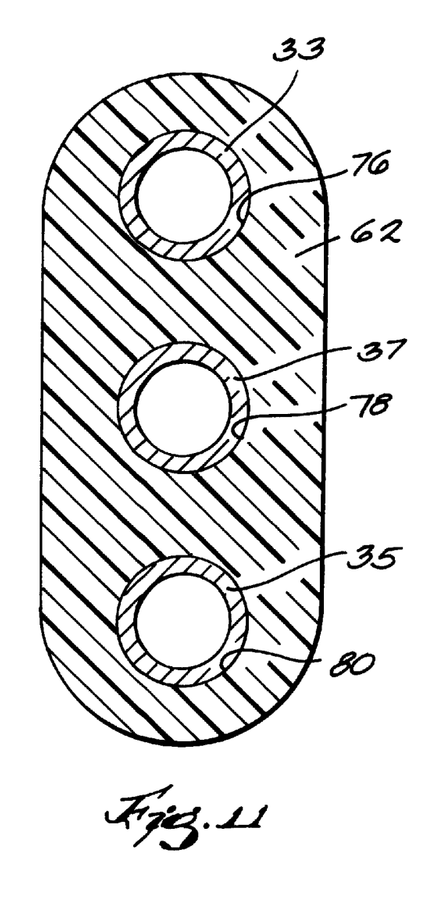
FIGS. 11, 12, and 13 are sectional views of the proximal end connector of FIG. 9 taken along lines 11—11, 12—12 and 13—13, respectively, of FIG. 9.
Figure 12:
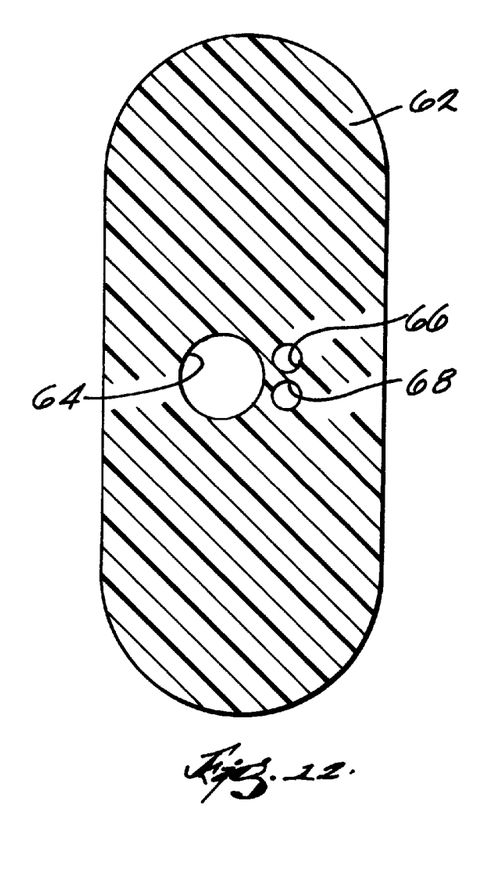
Figure 13:
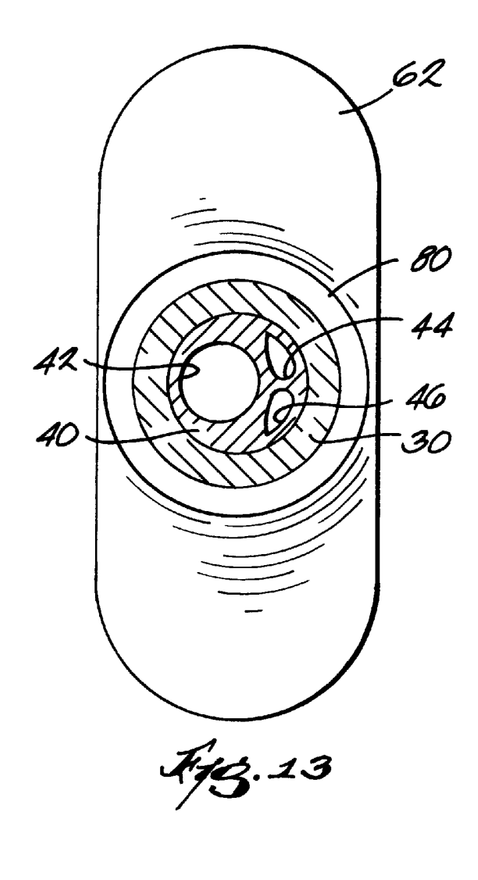

FIGS. 11, 12 and 13 are sectioned views of triangular connector 62 taken along lines 11—11, 12—12, and 13—13, respectively. FIG. 11 illustrates that tubes 33, 35 and 37 are secured to the inside walls 76, 78 and 80, respectively, of channels 66, 64, and 68, respectively.

FIG. 12 illustrates the molded internal configuration of channels 64, 66, and 68. Channel 64 is coupled to principal lumen 42 whereas channels 66 and 68 are coupled to secondary lumens 42 and 44, respectively.

FIG. 13 illustrates the details of connection between the principal and secondary lumens through strain relief 30. An optional shoulder 80 is molded into the narrower end of connector body 28. As shown, trilumen catheter body wall 40 is encircled by strain relief 30 and in turn merges into the small end of triangular connector body 62.

Figures 14, 15, 16:
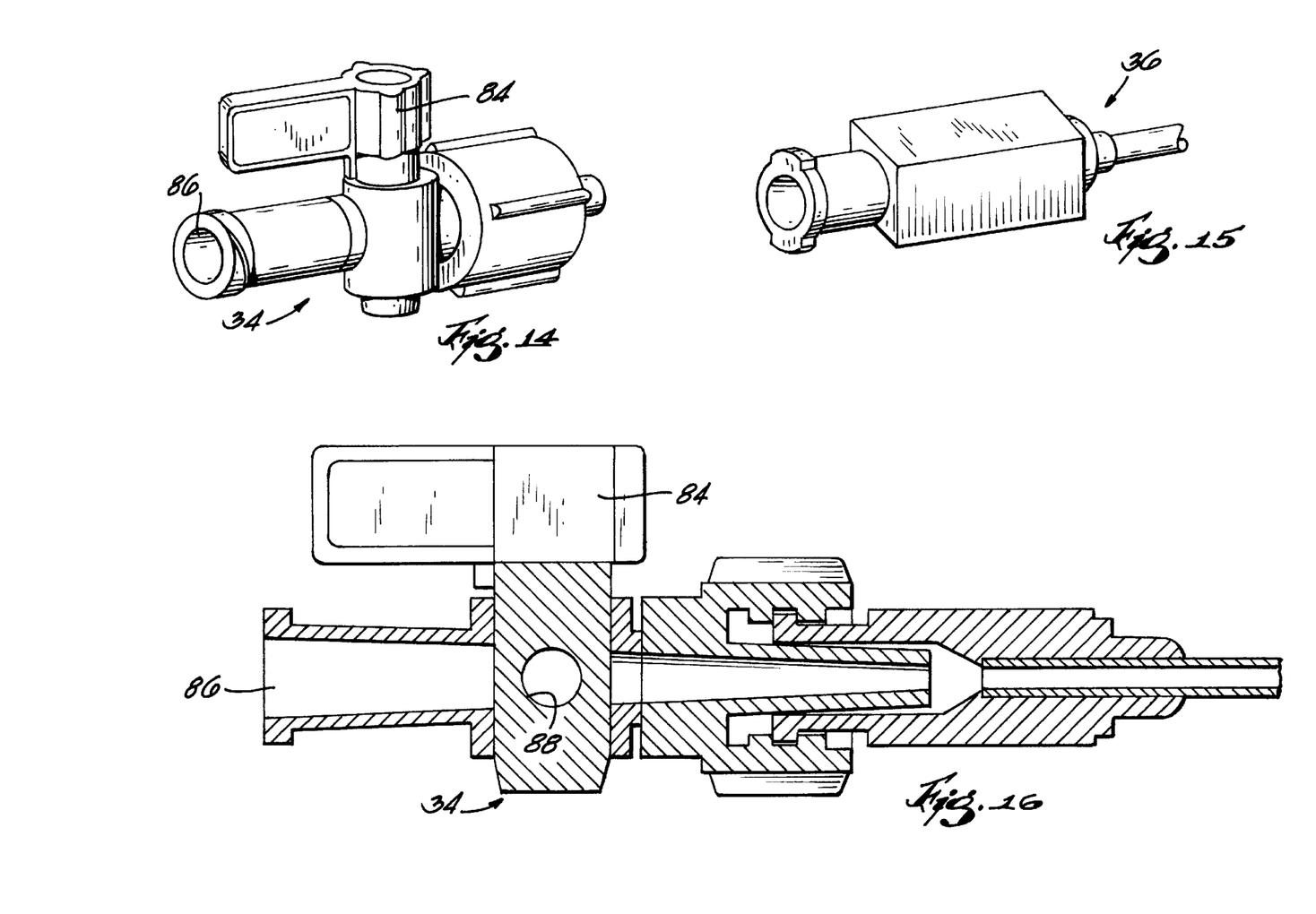
FIG. 14 is a perspective view of a proximal end connection for connecting a catheter of the invention with an external source of fluid with which to inflate distal end balloons.
FIG. 15 is a view of a proximal end connector for fluid for connecting a catheter of this invention to an external source of fluid with which to treat thrombus.
FIG. 16 is a sectional detail of the connector of FIG. 14.

FIGS. 14 and 15 illustrate perspective views of luer stopcock connector 34 as well as luer port connector 36. By means of valve or stopcock 84, luer connector 34 can be used to control fluid input and thereby control inflation and deflation of one or more balloons. Fluid is input at orifice 86 from an external source of fluid which is not shown. Generally speaking, an incompressible fluid such as saline solution will be utilized to inflate and control the radial dimension of balloons disposed on catheter body 12.

FIG. 15 illustrates a luer fitting connector 36 which permits thrombolytic fluid input as well as insertion of an occlusion means such as a tip occluder wire or a steerable occlusion wire (e.g., a guidewire) into primary lumen 42. The connector illustrated in FIG. 15 will be coupled to principal lumen 42 and, in turn, to all radial orifices 18 as well as the extreme distal end 14 of the catheter.

FIG. 16 illustrates in section the details of luer stopcock connector 34. As shown, valve or stopcock 84 has a transverse channel 88 which, when connected, can be used to control fluid input and output to balloons 20, 22 depending upon which lumen the luer stopcock connector 34 is connected.

As noted above, one aspect of this invention is a kit, the kit including a catheter as described above, a steerable guidewire alone or in combination with a non-steerable occluder wire. Steerable guidewires are well known to those skilled in the art of catheter utilization and will not be discussed in detail here. Particularly desirable steerable guidewires useable with the catheter described herein are commercially available from Lake Region Manufacturing of Chaska, Minn. Generally speaking, a guidewire useable with the present catheter comprises a stainless steel wire body and a coil spring distal tip. Useable steerable guidewires also preferably have coatings of Teflon PTFE or silicone (or both).

Figure 17:
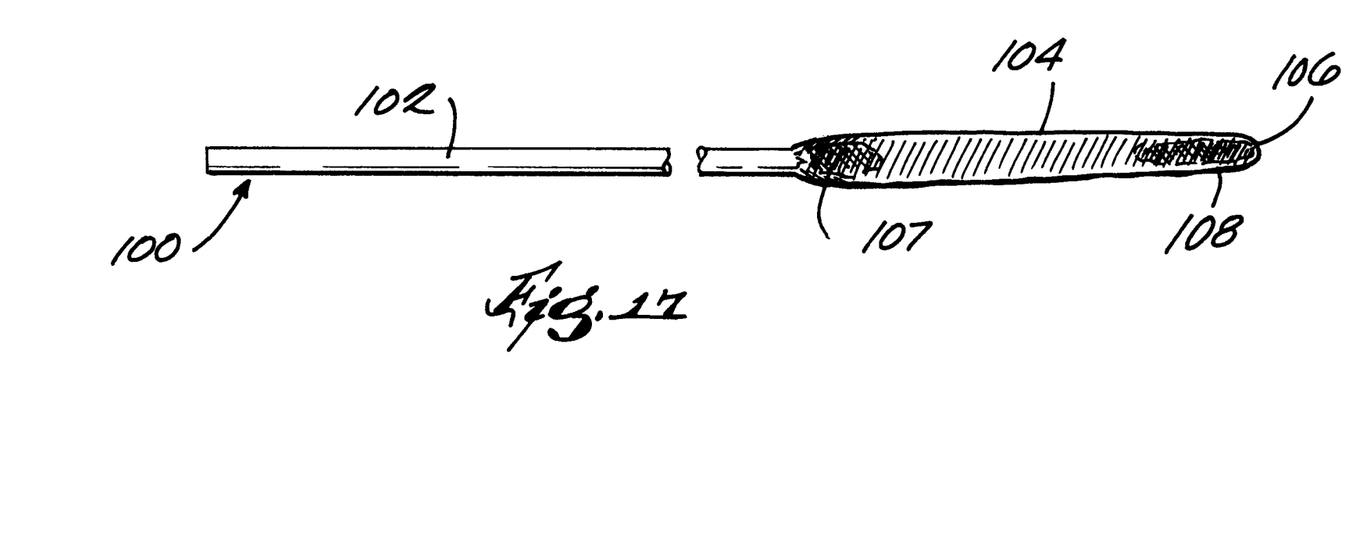
FIG. 17 is a schematic depiction of a steerable guidewire useable with this invention.
Figure 18:
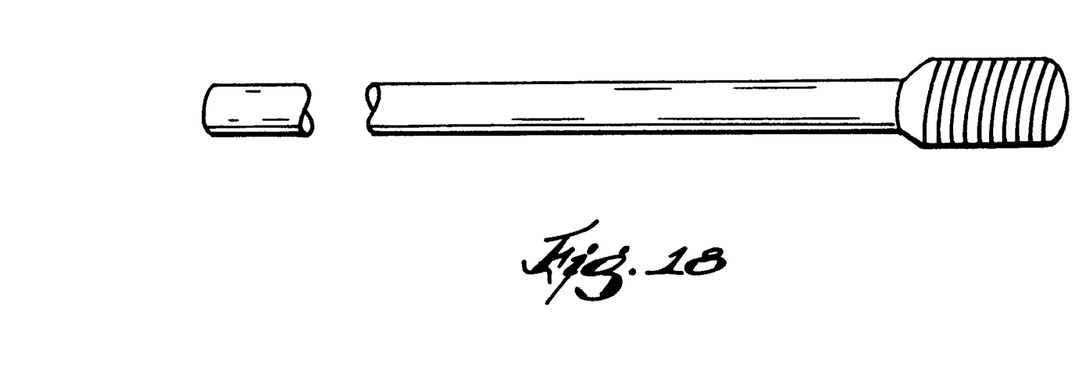
FIG. 18 is a schematic depiction of a tip occluder wire in accordance with this invention.
Figure 19:
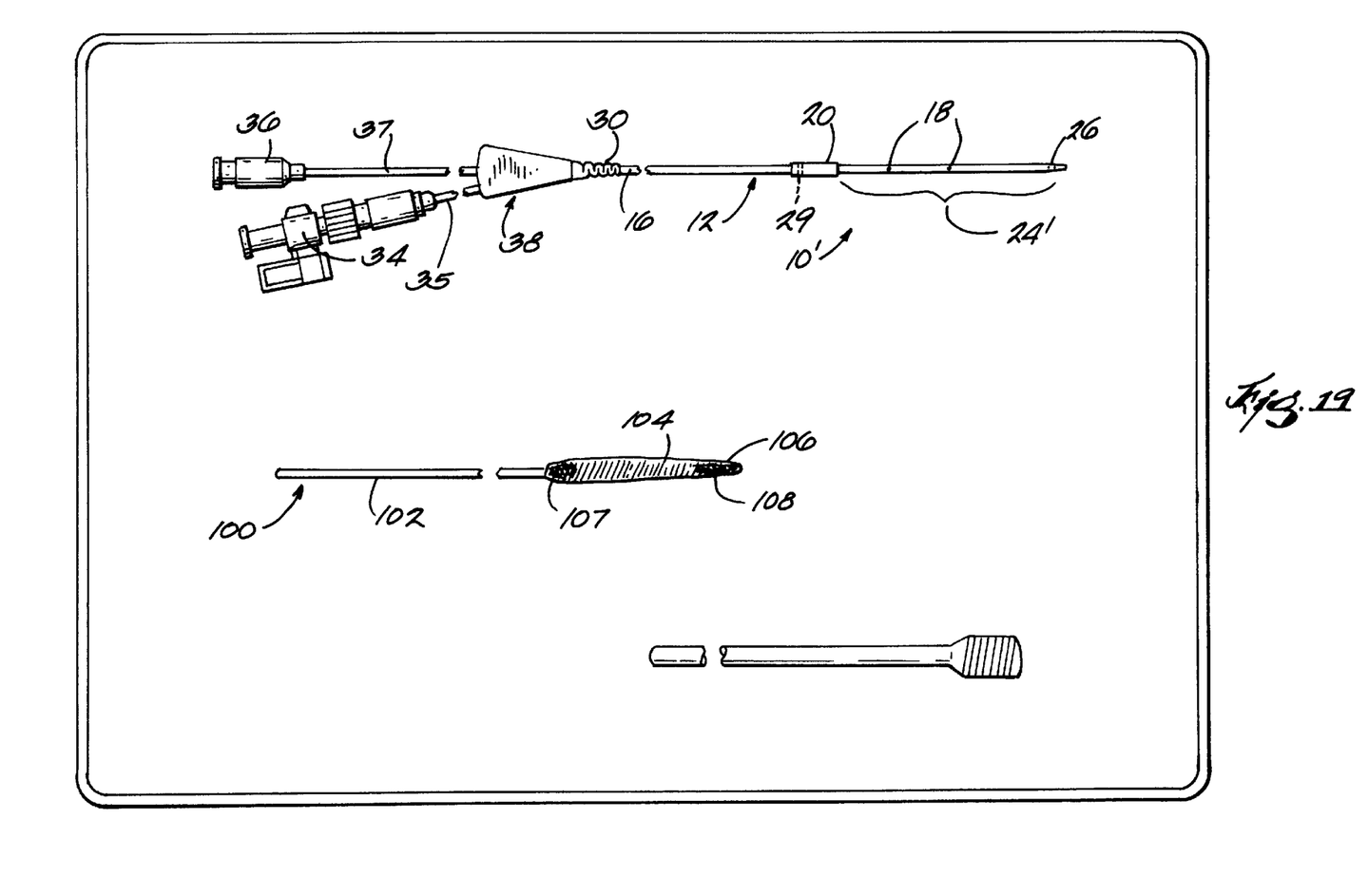
FIG. 19 depicts a kit of this invention.

FIG. 17 shows schematically a preferred structure of a steerable guidewire 100 usable with the present catheter. Guidewire 100 comprises a stainless steel core wire body 102 having a distal coil 104 (shown in partial section) on the end thereof. Core wire body 102 terminates in an atraumatic distal tip 106 which optionally may be made of a radiopaque material. A proximal radiopaque marker band 107, e.g., on the proximal end of coil 104, may be included in the structure depending upon user preference. Beneath coil 104 and located adjacent distal tip 106 additional radiopaque markers or radiopaque indicia, e.g., a radiopaque wire segment 108, may be included.

A kit of this invention can also include an occluder wire or catheter tip occluder. As described above, the tip of an occluder wire is enlarged to cooperate with the tapered or reduced diameter segment of the catheter body principal lumen to restrict distal fluid delivery and to force fluid infusion from radial orifices or side ports 18. An occluder wire usable with this invention will generally comprise a stainless steel wire body with a ball or enlargement formed or brazed to or proximate to its distal end. Diameters of the wire body may range widely from approximately 0.009 in. to about 0.018 in. Length also may vary from approximately 80 to 160 cm. The diameter of the stainless steel wire body should be small relative to the diameter of the primary lumen to provide more space for fluid to be infused therearound when the occluder wire is in position. A tip occluder wire will, generally speaking, not be steerable and will not normally be intended to exit the distal end of the catheter. As discussed above, this permits a catheter in which a tip occluder is used to be positioned closer to an obstruction.

A kit of this invention may also include an extension wire or an exchange wire. An extension wire is used, for example, to extend an already positioned guidewire (i.e., positioned within the vasculature) to facilitate catheter exchange. Extension wires generally comprise stainless steel and include a docking or mating distal segment which cooperates with a mating segment on the proximal end of the guidewire. While the docking or guidewire extension system utilized is not critical to this invention, a particularly desirable guidewire extension system is commercially available from the Lake Region Manufacturing Company of Chaska, Minn., U.S.A. The primary limitation on guidewire/ extension wire docking systems selection is that catheter exchange over the extended wire must be easily and quickly accomplished.

Lastly, depending upon the application and user preference, a kit of this invention may include various other components. For example, a Touhy-Borst "Y" Adaptor may be included. The hemostasis valve of such an adaptor prevents possible catheter leakage with a guidewire or occluder wire in place in the catheter. Touhy-Borst "Y" Adaptors are commercially available from several manufacturers. The kit may also include syringes (i.e., to be used to inflate the balloon or balloons), gloves, topical anesthetics and other equipment as needed for the application.

In another aspect, the present invention is a method of treating an obstruction, such as thrombus, within a vascular structure. (The location of the obstruction has been previously identified by methods well known to this art.) A method according to this invention comprises the steps of first advancing a steerable guidewire through the vasculature until the distal tip thereof is adjacent, i.e., in the vicinity or proximate to, the previously located obstruction or diseased segment to be treated. Next, a catheter having a structure as described above is advanced or slid over the guidewire until the infusion zone is located at the treatment site. At this juncture, the spatial relationship between the obstruction and the catheter/guidewire structure will determine the next step. If the steerable guidewire/catheter combination/structure cannot be positioned through the obstructed segment, then the guidewire is removed from the catheter and an occlusion means, occlusion wire, or tip occluder wire, is advanced through the primary lumen thereof. If the catheter/guidewire combination structure can be passed through the vascular obstruction, utilization of the steerable catheter guidewire/ combination continues. While utilization of the steerable wire is preferred, a non-steerable tip occluder wire permits the extreme distal portion of the catheter to be positioned more closely to, for example, thrombus which cannot be crossed with a steerable wire. Withdrawing a steerable guidewire from the catheter body, which would permit the catheter to be positioned more closely to the treatment site, tends to restrict radial fluid delivery due to restriction of diameter of the primary lumen. Both the steerable guidewire and the occlusion means or tip occluder wire have an enlargement adjacent their distal ends which cooperate with the reduced diameter portion of the primary lumen substantially to prevent fluid from passing distally from the catheter. Whether the tip occluder or steerable guidewire is used, the next step is to inflate the balloon means to define the treatment area. Lastly, thrombolytic agent is introduced into the primary lumen and subsequently exits or infuses from the radial passages to the infusion zone to treat the obstruction.

In a preferred practice of this method, the catheter includes a plurality of balloons located distally and proximally with respect to the orifices. The balloons are fluidically coupled to the proximal end of the catheter by means of secondary lumens which permit the balloons thereby to be inflated and deflated. Thrombolytic agents may include urokinase, streptokinase, tissue plasminogen activator (TPA), or a similar therapeutic species. As the lesion within the treatment area is exposed to the thrombolytic agent, some of the material is dissolved and is removed therefrom.

In a preferred practice of the above method, a radiopaque structure on the catheter, usually on its distal segment, is monitored while the catheter is positioned within the vasculature. A plurality of radiopaque structures, such as platinum rings or bands, may be disposed along the length of the catheter, and on the steerable guidewire and on the occluder wire. These structures appear more intense than adjacent, non-radiopaque materials under fluoroscopic examination. Generally, a steerable guidewire will have a radiopaque distal tip and possibly additional proximally-located radiopaque structures. By observation of these radiopaque structures, the progress of the catheter into the vasculature can be observed, the location of the balloon or balloons (and therefore the infusion zone) relative to the treatment site can be determined, and the relationship between the catheter and the guidewire or occluder wire can be monitored. Utilization of the cooperatively located radiopaque structures in catheter placement and in therapeutic application is a particularly advantageous aspect of the present methods.

Various modifications and alterations of this invention will become apparent to those skilled in this art from the above disclosure. It will be understood that all such variations and modifications within the spirit and scope of this invention are included within the scope of the attached claims.

What is claimed is:

1. A kit for the treatment of thrombus within a vessel of a patient the kit comprising:

a. An infusion catheter, the catheter having a fixed length, distal infusion zone and comprising a cylindrical catheter body comprising:
   i. a wall, the wall having;
   ii. distal and proximal ends, one of the distal and proximal ends having located thereon;
   iii. balloon means for isolating a treatment area within the vessel, the wall further including a plurality of radial orifices; the catheter body further defining;
   iv. a first interior lumen, said first lumen extending entirely through said catheter body to couple, fluidically, said distal and proximal ends of said body and said orifices, said first lumen having a larger diameter segment beginning at the proximal end of the catheter and a reduced diameter segment interiorly adjacent said distal end of said catheter body and distal to said orifices, said reduced diameter segment being adapted to cooperate with an occluder means to restrict fluid flow distally from the catheter;
   v. at least a second lumen, said second lumen being in fluid communication with said balloon means and said proximal end of said catheter body so as to permit said balloon means to be inflated thereby;

b. An occluder wire having an enlargement adjacent its distal end;

c. A steerable guidewire, the guidewire being adapted to position an infusion catheter within the vascular system.

* * * * *